United States Patent
Bietsch et al.

(10) Patent No.: US 7,891,295 B2
(45) Date of Patent: *Feb. 22, 2011

(54) PRINTING IN A MEDIUM

(75) Inventors: Alexander Bietsch, Rueschlikon (CH); Emmanuel Delamarche, Thalwil (CH); Bruno Michel, Adliswil (CH); Heinz Schmid, Waedenswil (CH); Heiko Wolf, Pfaeffikon (CH)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/249,322

(22) Filed: Oct. 10, 2008

(65) Prior Publication Data

US 2009/0038493 A1 Feb. 12, 2009

Related U.S. Application Data

(63) Continuation of application No. 10/527,277, filed on Aug. 4, 2005, now Pat. No. 7,434,512.

(30) Foreign Application Priority Data

Sep. 9, 2002 (EP) .................................. 02405777

(51) Int. Cl.
*B41M 9/00* (2006.01)
(52) U.S. Cl. ................ 101/483; 101/395; 101/401; 101/368
(58) Field of Classification Search ................ 977/887
See application file for complete search history.

(56) References Cited

U.S. PATENT DOCUMENTS

| 3,403,623 | A | * | 10/1968 | Blackwood ................ 101/368 |
| 4,539,747 | A | | 9/1985 | Stein |
| 5,669,303 | A | * | 9/1997 | Maracas et al. ............ 101/327 |
| 6,089,853 | A | | 7/2000 | Biebuyck et al. |
| 6,180,239 | B1 | | 1/2001 | Whitesides et al. |
| 6,355,198 | B1 | | 3/2002 | Kim et al. |
| 6,365,059 | B1 | * | 4/2002 | Pechenik ..................... 216/52 |
| 6,399,295 | B1 | | 6/2002 | Kaylor et al. |
| 6,908,861 | B2 | | 6/2005 | Sreenivasan et al. |
| 6,936,194 | B2 | | 8/2005 | Watts |
| 6,943,117 | B2 | | 9/2005 | Jeong et al. |

(Continued)

FOREIGN PATENT DOCUMENTS

DE 3225483 A1 5/1983

(Continued)

OTHER PUBLICATIONS

Bietcsh et al., "Conrofmal Contact and Pattern Stability of Stamps Used for Soft Lithogrpahy," Oct. 1, 2000, Journal of Applied Physics, vol. 88, No. 7, pp. 4310-4318.*

*Primary Examiner*—Daniel J Colilla
(74) *Attorney, Agent, or Firm*—Cantor Colburn LLP; Vazken Alexanian

(57) ABSTRACT

A method for transferring a pattern from an elastic stamp to a substrate in the presence of a third medium is described. A proximity contact is achieved between the stamp and the substrate. A layer of the third medium between the stamp and the substrate is controlled to a predetermined thickness. Stamps for carrying out this method are also described.

16 Claims, 15 Drawing Sheets

U.S. PATENT DOCUMENTS

2002/0050220 A1 * 5/2002 Schueller et al. ............ 101/486
2002/0098618 A1 7/2002 Rogers
2002/0159918 A1 10/2002 Tseng et al.
2006/0279018 A1 * 12/2006 Salleo et al. ................ 264/219

FOREIGN PATENT DOCUMENTS

DE 3201065 A1 7/1983

* cited by examiner

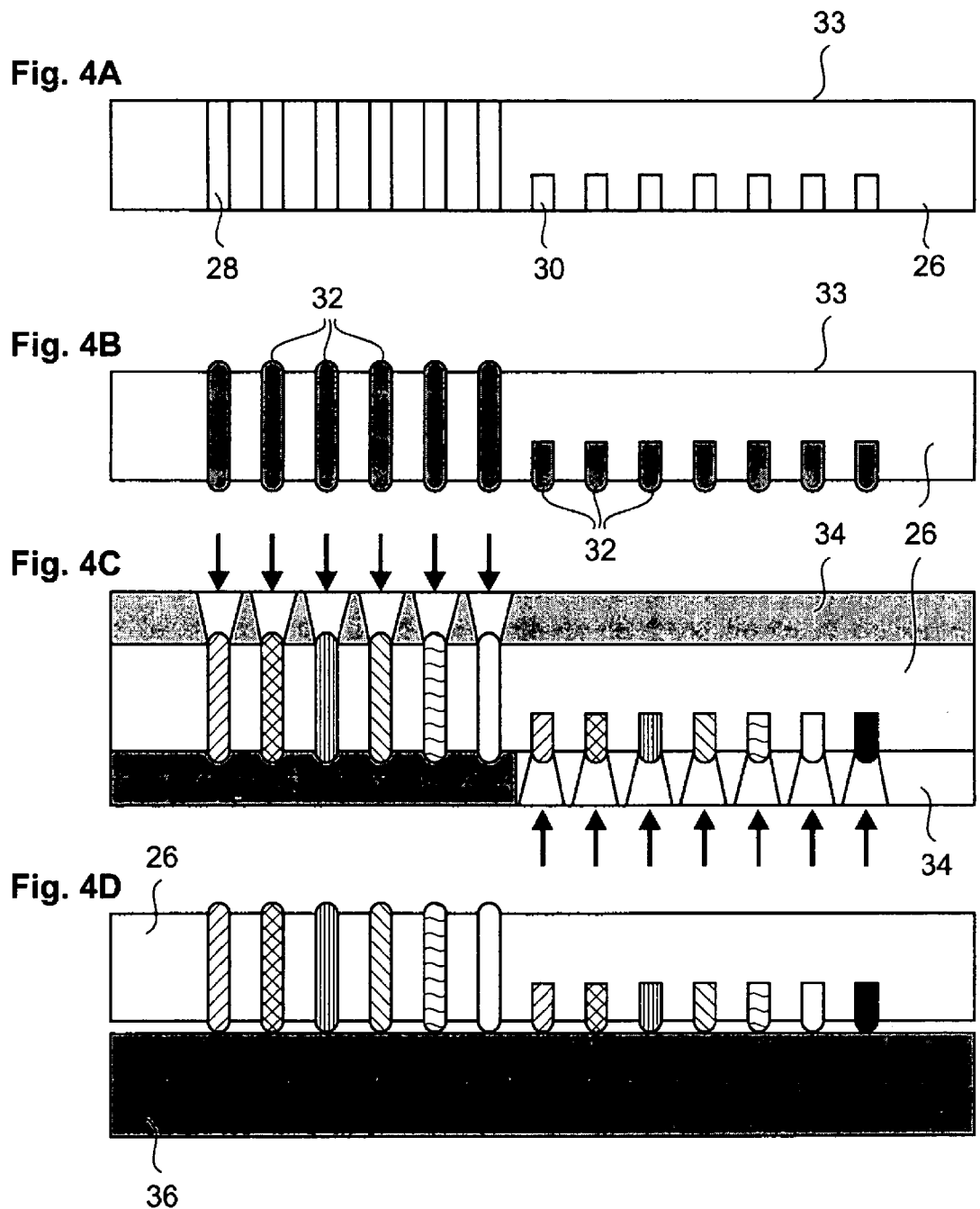

PRINTING IN A MEDIUM

CROSS REFERENCE TO RELATED APPLICATION

This application is a continuation of and claims priority from U.S. application Ser. No. 10/527,277, filed Aug. 4, 2005 now U.S. Pat. No. 7,434,512, which issued on Oct. 14, 2008. This application further claims priority from European Patent Application 02405777.0, filed on Sep. 9, 2002, the contents of which are incorporated herein by reference.

The present invention generally relates to printing and particularly relates to methods and stamps for transferring patterns to a substrate in the presence of a third medium.

Printing thin layers of ink or other material from a patterned surface is well known in the printing industry. Printing processes were originally developed for the exchange and storage of information adapted to human vision. This typically requires pattern and overlay accuracies down to 20 μm for acceptable reproduction. Printing processes have been used for other forms of patterning. For example, gravure offset printing has been used to make 50-μm-wide conductor lines on ceramic substrates and to pattern thin-film transistors in low cost display devices. Offset printing has been used for fabrication of capacitors and metal conductor lines as narrow as 25 μm Additionally, printed circuit board and integrated circuit packaging are popular applications of screen printing in the electronics industry. See, for example, B. Michel et al., IBM J. Res. Develop. 45, 697 (2001) and references therein.

Another conventional printing process is known as flexography. In flexography, a viscous ink is printed onto permeable materials such as porous paper, permeable plastic, and the like. Flexography is a rotary printing method involving resilient relief image plates to print images on materials that are difficult to print on with offset or gravure processes. Examples of such materials include cardboard, plastic films and substrates. Flexography is therefore used widely in packaging. Usually, the viscous ink prevents direct contact of the stamp with the substrate because it cannot be displaced quickly enough during fast printing operations. Transfer of a thick layer of ink is usually desired. However, this prevents replication of small feature sizes, typically smaller than 20 μm. See, for example, H. Kipphan, "Handbuch der Printmedien", Springer Berlin, 2000 and J. M. Adams, D. D. Faux, and J. J. Rieber, "Printing Technology 4th Ed.", Delamare Publishers, Albany, N.Y.

Micro contact printing uses a similar stamp to that used in flexography, but typically transfers a mono layer of ink onto an impermeable surface. A more general process called soft lithography has been applied to printing thiols and other chemicals onto a range of surfaces. Typically, the chemicals are first applied to the stamp as solutions in a volatile solvent or via a contact inker pad. After inking and drying, molecules in the bulk and surface of the stamp are in a "dry" state. The molecules are transferred by mechanical contact. The stamp is typically formed from poly-(dimethyl)siloxane (PDMS). See, for example, B. Michel et al. "Printing meets lithography", IBM, J. Res. Develop. 45 (5), 697 (2001)).

Micro contact processing, soft lithography, and flexography involve locally defined, intimate contact without voids between stamp and substrate. This is generally known as conformal contact. Conformal contact comprises macroscopic adaptation to the shape of the substrate and microscopic adaptation of a soft polymer layer to a rough surface.

Micro array technology is expected to accelerate genetic analysis. Micro arrays are miniature arrays of gene fragments or proteins attached to or deposited on glass chips. These so-called "biochips" are useful in examining gene activity and identifying gene mutations. A hybridization reaction is typically used between sequences on the micro array and a fluorescent sample. In a similar manner, protein markers, viruses, and protein expression profiles can be detected via protein specific capture agents. After reaction, the chip is read with fluorescence detectors. The intensity of fluorescing spots on the chip is quantified. The demand for micro arrays and techniques for fabricating micro arrays is increasing. Conventional methods for patterning biological molecules onto biochips are described, for example, in M. Schena, "Micro array Biochip Technology", Eaton Publishing, Natick Mass., (2000). In a first conventional method, a surface is treated with compounds in a sequential manner by: pipetting with a pipetting robot or capillary printing; dispensing droplets with an ink jet; or, patterning with a pin spotter. In a second conventional method, a surface is patterned with molecules in parallel thus reducing manufacturing cost. Microfluidic networks, capillary array printing, or micro contact processing can be employed in implementation of the second method.

The printing of biological molecules and water soluble catalysts by conventional techniques does not always work, is difficult to reproduce, and results are variable. Repetitively creating homogeneous prints with high yield over large areas is very difficult, particularly if the molecules require permanent hydration. See, for example, A. Bernard et al., "Micro contact Printing of Proteins", Adv. Mater. 2000 (12), 1067 (2000). Many biological molecules require at least partial hydration. Also, many biological processes operate only when there is liquid to provide mobility. When molecules are to selectively perform chemical reactions on a surface in a patterned fashion, it is desirable to fix the molecules in place to avoid blurring the pattern by spreading. In catalytic printing therefore, it would be desirable to tether molecules so that they can reach the surface only where desired. Limited mobility should be permitted so that molecules can function effectively without escaping. Biological molecules preferably encounter the substrate while immersed in a layer of water to permit a chemisorption reaction. Because chemisorption reactions of proteins are not selective and many potential anchoring groups may be present on the substrate, mobility requirements are lower. For molecule-molecule interactions, control over hydration is desirable. One way to prevent drying without immersion in water is to work in saturated air. In many printing operations, this is helpful. However, the humidity level is difficult to regulate. Molecules can interact creating adhesion detectable with an adhesion sensor as described, for example, in EP 0 962 759 A1. For example, an antibody and its matching antigen may interact. Similarly, a DNA oligomer may hybridize with its complementary oligomer.

Other printing technologies include Ultra Violet (UV) lithography or UV-molding. In such techniques, a patterned glass master is pressed into a liquid prepolymer. The prepolymer is then cured and solidified by exposure to UV light. See, for example, M. Colburn et al., "Patterning nonflat substrates with a low pressure, room temperature imprint-process", J. Vac. Sci., Technol. B. 6, 2161 (2001). On release, the pattern formed in the polymer is a replica of the master. However, it is difficult to displace such a polymer on large areas to achieve a pattern with acceptable definition. There is usually a residual layer left. Use of an identically patterned elastomeric stamp in place of glass provides similar replication except for two differences, as follows. Experiment indicates that in protruding areas of the stamp, where the polymer was to be displaced down to the surface, localized dome-like protrusions of trapped material were discovered. Secondly, variation was observed in the thickness of features molded from the recesses in the stamp Typically, the thickness of each feature was smaller in its center. The depth of depression was proportional to the load applied to the stamp. See, for example, Bietsch and Michel, "Conformal contact and pattern stability of stamps used for soft lithography", J. Appl. Phys. 88, 4310 (2000); Johnson, "Contact Mechanics", Cambridge University Press, Cambridge (1985); and S. P. Timoshenko and J. N. Goodier, "Theory of Elasticity", Mc-Graw-Hill, New York). Formulae for the displacement of liquids can be derived from lubrication theory. See, for example, A. Cameron, "Basic Lubrication Theory" Wiley, New York (1981)).

Hydrogels are used in gel electrophoresis. Because hydrogels are flexible, they are also used as stamp materials for printing of biological molecules. See, for example, D. Brett et al., Langmuir 14, 3971 (1998) and Langmuir 16, 9944 (2000); M. A. Markowitz et al., Appl. Biochem. and Biotechnol. 68, 57 (1997). Hydrogels are mainly composed of water, and water easily diffuses through a hydrogel matrix. Thus, hydrogels avoid hydration problems associated with PDMS based printing. However, hydrogel stamps change volume on exposure to water or upon drying. Also, molecules can diffuse between protrusions of the stamp. Hydrogel stamps for parallel printing of different molecules with good registry and separation among the spots have yet to be demonstrated.

Printing of biological molecules from an affinity stamp with catalysts and of hydrophilic molecules from a hydrophilized PDMS stamp onto a substrate have both been demonstrated on a research level but are more difficult to implement commercially where areal transfer over large surfaces is desired. The difficulty arises either because there is not enough of the third medium required for hydration chemisorption, or hybridization on the substrate or because there is too much third medium, preventing intimate contact and transfer. Third medium herein is the general expression for a medium in which other components are carried. Depending on the application, the third medium may be a gas, water, solvent, or polymer. See, for example, A. Bernard et al., "Affinity capture of proteins from solution and their dissociation by contact printing", Nature Biotechnol. 19, 866 (2001).

A third medium in the form of damping water is found in offset printing of viscous inks onto impermeable substrates. See, for example, J. M. Adams, D. D. Faux and J. J. Rieber, "Printing Technology 4th Ed." Delamare Publishers, Albany, N.Y., 1996. Offset printing typically employs a printing cylinder having a rubber printing surface. Prior to application of ink, the surface is moistened. This transfers a thin layer of detergent carrying water to the printing surface. The detergent reduces surface tension in the water. The water layer covers the surface but can be displaced by application of patterned link. A water layer improves definition in printing processes where information on a master is presented as a wettability pattern. The water layer prevents incursion or adherence of ink to ink repelling regions. In transfer from the printing surface to paper, water is absorbed into the fiber mesh of the paper and dried. This process does not work on impermeable materials. In such cases, the printing rubber surface slips on the water layer and the pattern is smeared. A conventional solution to this problem is to roughen the surface to be printed and render it hydrophilic. By controlling the thickness of the water layer, fluid transport over large areas can be prevented. This avoids need for capillary channels that obstruct printing of pictures. Roughening also determines fluid resistance in percolating channels and therefore determines printing speed. Roughening creates a random distribution of peaks and troughs. These lead to unobstructed percolation path between larger zones. The random process is however inefficient because it also creates many disconnected capillary paths.

A third medium also affects high speed contact between a rigid object and an adhesive tape in a gas such as a air. The gas can build considerable pressure between the object and the tape. The pressure deforms the tape to create a central depression. The depression causes trapping of an air pocket. The air pocket prevents accurate positioning of the object in subsequent process steps such as pick and place operation in the manufacture of semiconductor subassemblies, disk read/write heads, and the like. Such assembly is increasingly important as semiconductor technology moves from creating entire processors on one chip towards assembling sub-components on intermediate carriers. To assemble and process several chips in parallel, in flip chip bonding for example, typically requires pre-assembly on an adhesive tape or pad.

Self-assembly of µm-sized components on a chemically patterned surface in a third medium is typically a slow process in which particles approach the target surface closely enough to allow specific molecular or chemical interactions. Typically, such a process requires vigorous agitation to provide particles with sufficient diffusion through the third medium to establish contact with counterparts on the surface. It can be difficult to separate the particles when the third medium is not present. For assembly, it is desirable to have an intermediate interaction between the parts to be assembled to better control assembly. Appropriate placement produces stronger interaction, while inappropriate placement provides produces weaker interaction. For faster and more predictable assembly, an improved approach process for micrometer to millimeter sized particles in a third medium would be desirable. The third medium helps suspend particles that would otherwise affected by gravitational forces. In accordance with the present invention, there is now provided a method for transferring a pattern from an elastic stamp to a substrate in the presence of a third medium, the method comprising: controlling a layer of the third medium between the stamp and the substrate to a predetermined thickness.

In a preferred embodiment of the present invention, the substrate is rigid. In a particularly preferred embodiment of the present invention, the substrate is impermeable. The third medium may comprise one or more of gas, water, solvent, polymer, emulsion, sol-gel precursor, and the like. The controlling may comprise avoiding trapping of the third medium via the stamp matrix being permeable to the third medium. Alternatively, the controlling may comprise forming a nanometer sized gap in the stamp filled with the third medium.

The controlling preferably comprises providing a patterned stamp surface having channels to drain the third medium. In a preferred embodiment of the present invention, the controlling comprises filling vias and recesses formed in the stamp with a component having an affinity for the third medium. The component may be hydrophilic. The component preferably comprises a gel. The gel is preferably swellable by the third medium. The controlling preferably comprises swelling the gel with the third medium to form protrusions in the stamp. In a particularly preferred embodiment of the present invention, the controlling comprises providing an array of protrusions and recessed zones in the stamp. The controlling may comprise guiding excess third medium away from the surface of the stamp via the recessed zones. The array preferably comprises a micrometer-sized pattern subdivided into smaller structures. The smaller structures may be separated by smaller drainage channels. The smaller drainage channels are preferably connected to a network of larger drainage channels. The third medium may be trapped in a shallow lense-like pocket between the stamp and the surface of the substrate. The controlling may comprise trapping the third medium in a pocket between the stamp and the substrate. The stamp may comprise channels. The channels define molecular sized gaps between the stamp and the substrate.

The present invention also extends to: use of such a method for printing biological molecules on a surface; use of such a method for printing dyes on a surface; use of such a method for printing catalysts on a surface; use of such a method for printing acids or bases on a surface; use of such a method for printing of radical initiators on a surface; use of such a method for detection of molecules through proximity by fluorescence resonance transfer; use of such a method for purification and concentration of reactants; use of such a method in an offset printing process; or use of such a method in a rolling contact process.

Viewing the present invention from another aspect, there is now provided a stamp for transferring a pattern to a substrate in the presence of a third medium, the stamp comprising a contact surface and drainage channels formed in the contact surface.

The surface is preferably patterned. The stamp may comprise an array of protrusions. The patterning may comprise a micrometer sized pattern subdivided into smaller structures. The drainage channels preferably extend between the smaller structures. The drainage channels preferably form a network.

Viewing the present invention from yet another aspect, there is now provided a stamp for transferring a pattern to a substrate in the presence of a third medium, the stamp comprising a permeable hydrophilic matrix. The stamp may comprise active vias. The vias may be filled with a material permeable by a third medium. The stamp may additionally or alternatively comprise active recesses. The recesses may also be filled with a material permeable by a third medium.

In a preferred embodiment of the present invention, there is provided a method for providing controlled contact between two articles that allows transfer with spatial control of a material from a stamp to a substrate in the presence of a third medium. In a particularly preferred embodiment of the present invention, there is provided a method that allows controlled formation of nanometer sized gaps filled with the third medium within which molecular processes can occur. In an especially preferred embodiment of the present invention, there is provided a method for providing conformal or proximal contact either induced by an external force or spontaneously in self-assembly. In a preferred embodiment of the present invention, there is provided a method wherein controlled proximity of an article to a substrate produces patterning of the surface with biomolecules or other molecules.

BRIEF DESCRIPTION OF THE DRAWINGS

Preferred embodiments of the present invention will now be described, by way of example only, with reference to the accompanying drawings in which:

FIGS. 4A to 4D are cross sectional views of a stamp embodying the present invention;

DETAILED DESCRIPTION OF THE PREFERRED EMBODIMENTS

Problems associated with printing from a stamp to a solid impermeable substrate by conformal or proximity contact can stem from an excess of a third medium such as a solvent. The excess prevents intimate contact and transfer because it forms a gap between the stamp and the substrate. The gap is filled with the excess thus preventing conformal contact. Problems can also arise if there is a lack of third medium on the substrate. Hydration, chemisorption and/or hybridization on the substrate can then be adversely affected. For example, biomolecular and chemical reactions usually require a third medium such as a solvent to function. In the first case, it is desirable to control the amount of the third medium to a well defined layer thickness. In a preferred embodiment of the present invention, this is achieved by providing drainage channels in the stamp surface. In the second case, it is desirable to offer a controlled amount of the third medium to the substrate. In a preferred embodiment of the present invention, this is achieved via a permeable stamp matrix.

The physics underlying printing in the presence of a third medium can be further understood by considering a flat stamp approaching a flat surface. The relation between gap height h and pressure p in compressed medium of viscosity η is described by Reynold's equation. See, for example, A. Cameron, "Basic Lubrication Theory", Wiley (New York 1981), Chapter 3.7. In the following example, a one-dimensional model is used. Reynold's equation thus simplifies to:

$$\frac{d}{dx}\left(\frac{h^3}{\eta} \cdot \frac{d}{dx}p\right) := 12 \cdot \frac{d}{dt}h \qquad (1)$$

where x is the coordinate parallel to the surfaces and t is time. The model can be applied to elongate surfaces. Examples in the data storage field include thin film head sliders. Typical dimensions of such sliders are 1.2 mm×50 mm. For squarer geometry, pressure may be reduced by a factor of around 2.

If both stamp and surface are rigid, h is independent from x. The differential equations for p and h can be solved. Thus, the origin is chosen in the middle of the surface of width w.

$$p(x) := \frac{3}{2} \cdot P \cdot \left[1 - \left(\frac{2 \cdot x}{w}\right)^2\right] \quad (2)$$

Figure 1A:
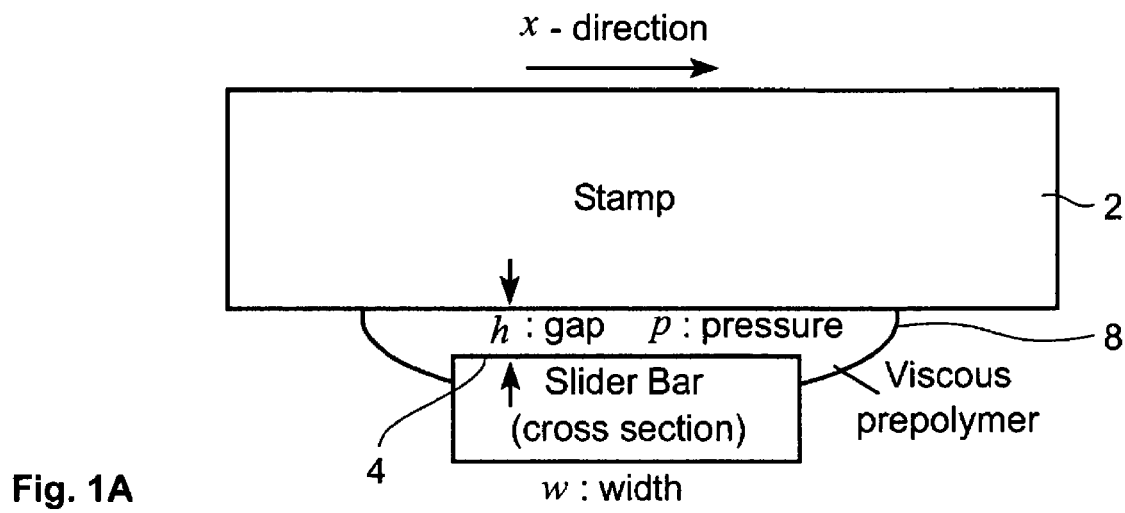
FIG. 1A is a side view of a stamp approaching a slider bar and an intervening viscous polymer.
Figure 1B:
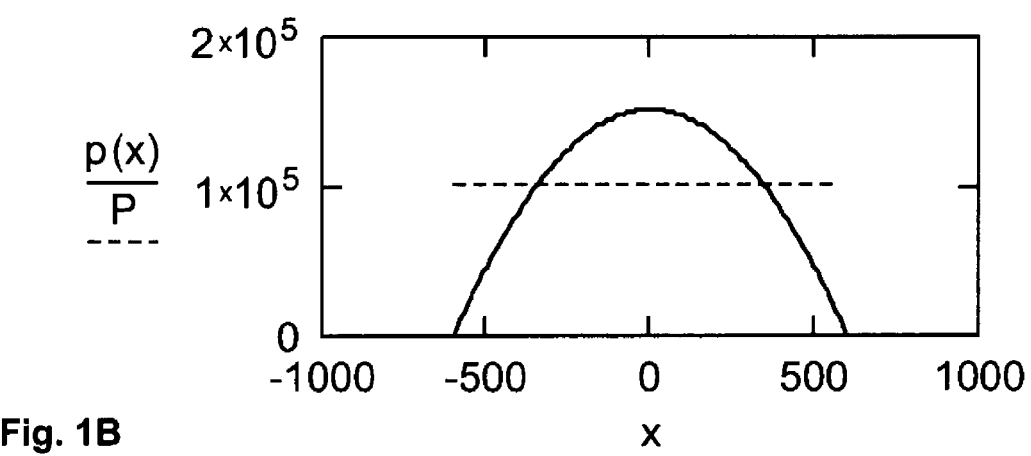
FIG. 1B to 1E are graphs showing pressure as a function of lateral position of the stamp and gap height.

FIG. 1A is a cross section of a stamp 2 and slider 4 with an intervening third medium 8. FIG. 1B shows that the pressure profile has a parabolic shape having a maximum in the center and dropping to zero at the edges. The maximum is 1.5 times the mean pressure P.

In practical implementations, either the stamp 2 or the surface 4 is elastic. The aforementioned pressure distribution causes a concave elastic deformation in the elastic part. This can lead to pockets trapping the third medium during contact. These trapped areas of the third medium are referred to as "pancakes". The normal deformation can be calculated from the pressure distribution based on a formula derived by Bietsch and Michel in "Conformal contact and pattern stability of stamps used for soft lithography" J. Appl. Phys. 88, 4310 (2000). For a slider geometry, a mean pressure of 1 bar can lead to concave depressions up to 10 μm in a typical silicone elastomer having a Young's modulus of 3 MPa. The deformation scales with the Young's modulus. A harder material reduces pancakes. In the case of slider processing, the slider 4 is rigid and the stamp 2 is elastic.

The pressure and gap height during the approach are closely related. There are two cases. The first case is constant applied load. The second case is constant speed of approach.

When constant load is applied, there is a constant pressure distribution according to equation 2. P is the mean pressure acting on the surface 4. The gap height is then calculated from equation 1:

$$h := \sqrt{\frac{\eta \cdot w^2}{2 \cdot P \cdot t}} \quad (3)$$

Figure 1E:
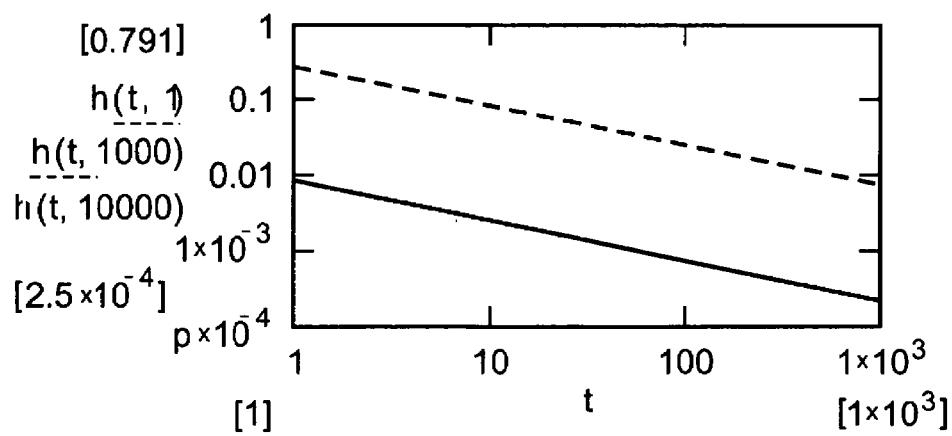

The calculations provide an estimate of how fast the third medium 8 is displaced by the stamp 2. The third medium may be a viscous prepolymer, gas, water, or a solvent. FIG. 1E shows decrease of gap height for different fluids of viscosities 100 cP, 1000 cP and 10000 cP at 1 bar applied load as a function of time. The viscosities are typical for UV-cureable polymeric materials. A gap as small as 1 μm is achieved for 100 cP within 1 s. However, a time of 100 s is required for the higher viscous material of 10000 cP.

In the second case of constant approaching speed, there is increasing pressure when the gap height is decreasing. This effect depends on viscosity, the speed (v) and the dimension of the punch.

$$p := \frac{4 \cdot \eta \cdot v \cdot w^2}{h^3} \quad (4)$$

where p is the mean pressure. FIG. 1C shows pressure as a function of gap height for a slider, when the third medium is water and the speed of approach is 10 μm/s. If the third medium is air, having a 60 times lower viscosity, this diagram is true for a speed of 600 μm/s. In this example, the pressure increases from moderate values (100 Pa) for a gap width "w" of 10 μm to values greater than $10^5$ Pa (=1 bar) when the gap is reduced below 1 μm.

Figure 1D:
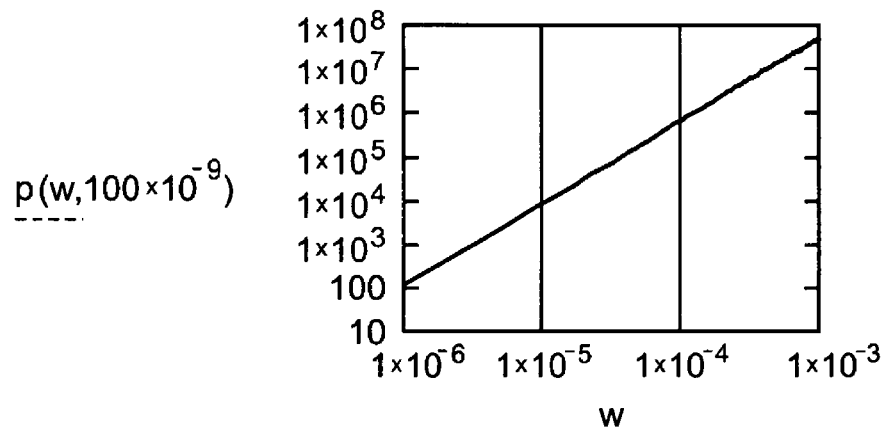
Figure 1C:
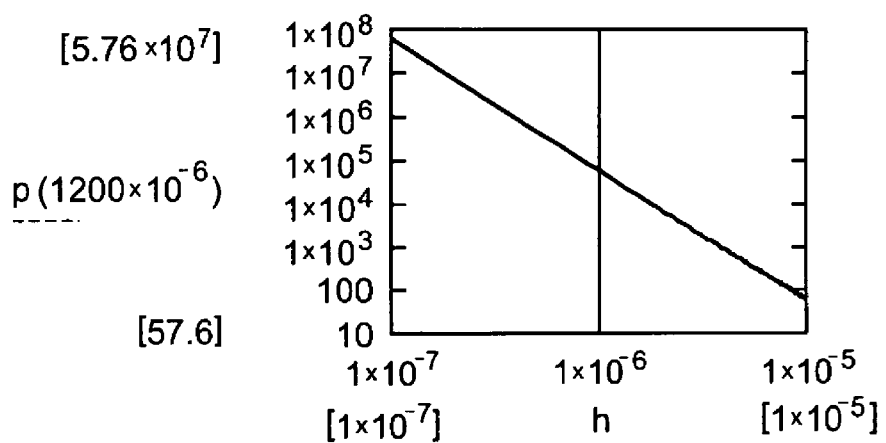

FIG. 1D shows how the pressure depends on the dimension of the surface 4. At a gap width of 100 nm the pressure is reduced to 50 Pascal for a width of the surface 4 of 1 μm compared to 50 MPa for a typical slider geometry of 1.2 mm. The maximal pressure scales with the inverse square of the stamp or surface size.

Figure 2A:
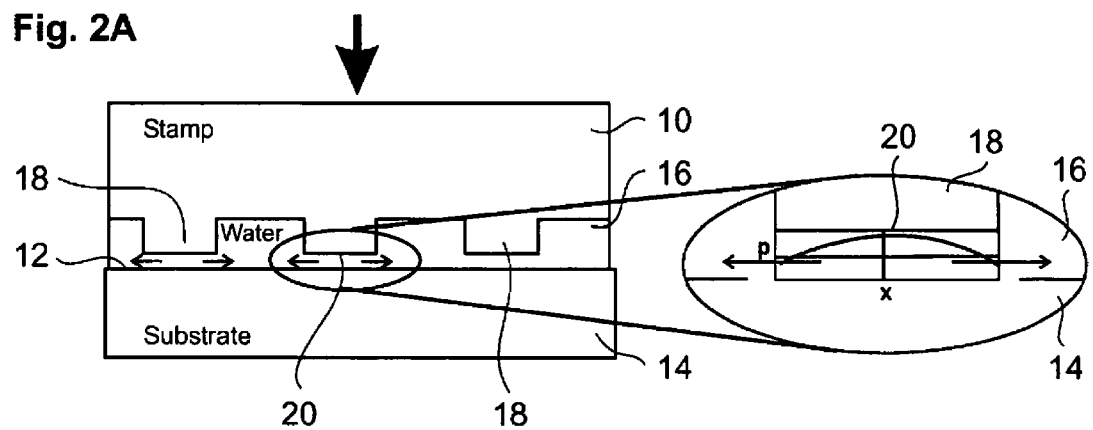
FIGS. 2A to 2B are side views of a stamp approaching a substrate in the presence of a third medium in liquid form.
Figure 2B:
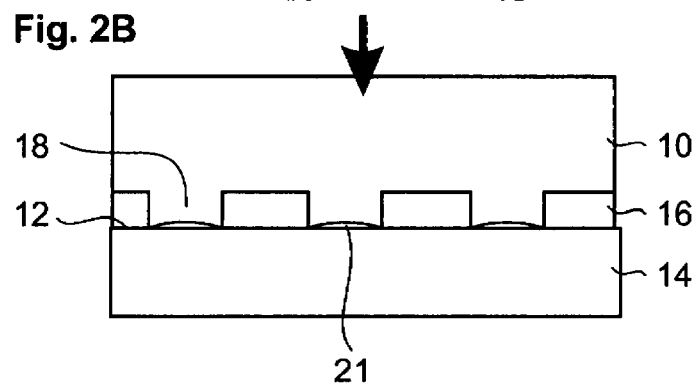
Figure 2C:
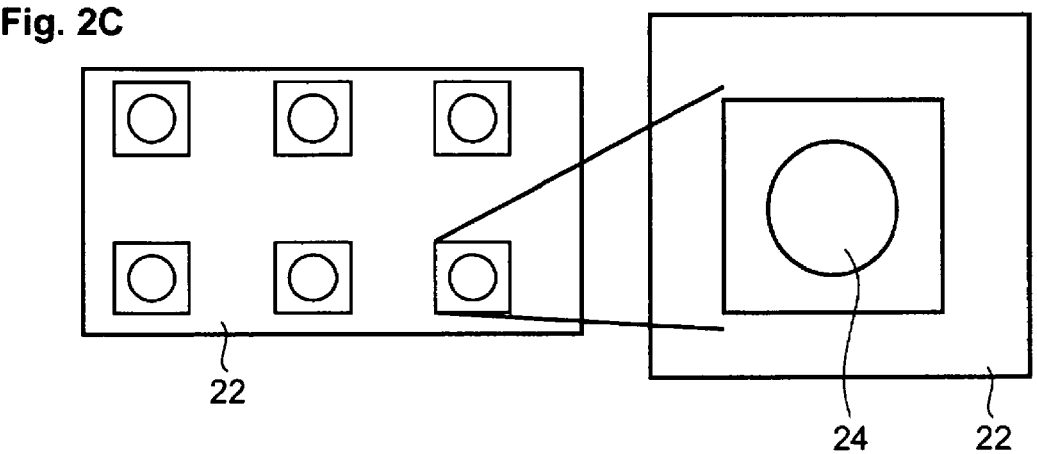
FIG. 2C shows photographs of the stamp in contact with the substrate.
Figure 3:
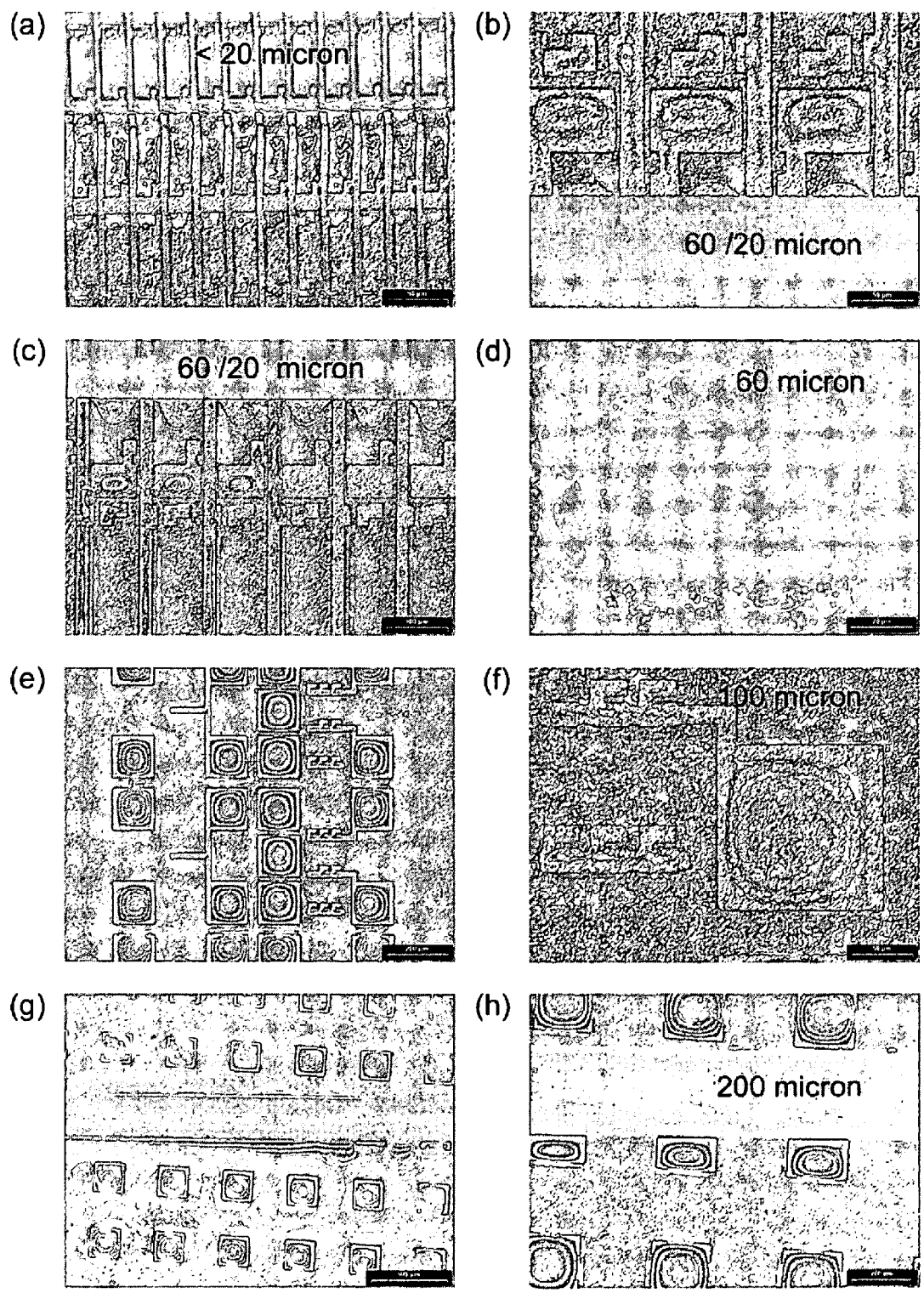
FIGS. 3A to 3H are photographs of interference fringes produced by quadrilateral patterns on the stamp when in contact with the substrate.

According to Bietsch and Michel, "Conformal contact and pattern stability of stamps used for soft lithography" J. Appl. Phys. 88, 4310 (2000), stamps deform under constant pressure to form so called "sagging" profiles. FIG. 2A shows an elastomeric stamp 10 approaching a rigid surface 12 of a substrate 14 in a third medium 16, such as water. The third medium 16 is displaced between the protruding features 18 of the stamp 10 and the substrate 14. See the arrows in FIG. 2A. When the gap between the stamp 10 and the substrate 14 becomes very small, the third medium 16 cannot be displaced instantly. Pressure thus builds up with a maximum below the center of the features 18. See the inset of FIG. 2A. The pressure build up elastically deforms the surface 20 of the features 18. When the stamp 10 contacts with the substrate 14, a lens-like pocket 21 of the third medium is trapped below each feature 18. See FIG. 2B. The profile follows the pressure distribution in the squeezed third medium 16. See again FIGS. 1B and 2A. FIG. 2C shows photographs of pancakes of water between an elastic hydrophilic stamp and a rigid glass surface 22. In this example, the stamp has square protrusions 24 of size 200 μm molded in Sylgard® 184. The stamp was pressed onto the surface 22 with a relatively low pressure of approximately 0.05 bar. This produces a load of 5000 Pa×fill factor, where fill factor is represented by the contact area divided by the overall area. Interference fringes in the form of Newton rings 24 are present. From the Newton rings 24 and the measured refractive index of 1.3, a maximal thickness of 350 nm of enclosed water 16 was estimated. The weak definition of the Newton rings 24 did not allow exact determination of the thickness as a function of protrusion size. To demonstrate the effect with more definition, experiments with UV-curable pre polymers as a third medium were conducted. The results of these experiments are summarized in FIGS. 3A to 3H. FIGS. 3A to 3H show photographs of interference fringes on quadratic patterns having sizes of <20, 20, 60, 100, and 200 μm, where the term "60/20 microns" describes the width of features in μm. In FIGS. 3E and 3G, deformation of elastomeric protrusions is measured. FIGS. 3E and 3G show the same structures as FIGS. 3F and 3H but with a larger view. Thickness analysis as a function of pattern size showed a linear size dependence having an intercept close to 0 and a slope of 4 nm per μm pattern size. This shows that the enclosed layer thickness linearly scales with pattern size. A comparison of trapped third medium and the layer on the 200 μm square protrusions shows a difference of a factor 3. This is attributed to the viscosity difference between water and the UV-curable prepolymer. Based on these results, a stamp for direct contact with no water (e.g., a layer <1 nm) should have patterns with sizes smaller than 1000 nm. On the other hand, it is also possible to choose larger features to create gaps with defined thickness. Based on these results, a controlled layer transfer over a gap of 4 nm, for example, can be performed by selecting protrusions with 3 μm size, and a pattern transfer over 20 nm can be performed by selecting protrusions with 250 μm size.

Flow resistance in fluidic networks scales with the inverse of smallest channel dimension and with channel length. Capillary force also scales with the inverse of channel dimensions. Fluid mechanics allows scaling of networks to nanometer dimensions. However, patterning with these networks is restricted by surface to volume ratio. A large surface permits molecules dissolved in a liquid to encounter the surface and react accordingly. This leads to depletion of the liquid. Capillary networks are therefore very efficient in patterning via relatively short channels with channel dimensions in the micrometer regime. See, for example, Delamarche et al., "Microfluidic networks for chemical patterning of substrates: Design and application to bioassays", J. Am. Chem. Soc. 120, 500 (1998). When dimensions are in the nanometer scale, molecules are preferably brought to desired locations by other means. However, networks can still guide fluid to and from different zones. In immersed systems with no liquid/air interface present, capillary forces are immaterial. In this case, flow resistance is approximately proportional to the product of channel length and inverse normalized channel dimension, $(w+h/(w*h))^2$, where w is the width and h is the height of the channel. Scaling branched fluidic networks to the nanometer scale involves channels with different orders of magnitude: channels with small dimensions for short paths; channels with medium dimensions for intermediate paths; and, channels with large dimensions for long paths. Combining two or three layers of appropriately sized channels allows guidance of fluids from macroscopic to nanoscopic dimensions in a perfusion system or from nanoscopic to macroscopic dimensions in a drainage system. This is similar to the human blood circulation system, in which several nested subsystems are used to scale from meters in arteries with pumped flow to nanometers in cell gaps.

Efficient biological printing and catalytic conversion involves definition and control of a thin layer of solvent between stamp and substrate. This is not however physically stable in conventional systems. See, for example, A. Martin et al., "Dewetting nucleation centers at soft interfaces", Langmuir 17, 6553 (2001), describing the spontaneous dewetting of a meta stable liquid film on an elastomeric surface. In a first embodiment of the present invention, this problem is solved by avoiding the unwanted trapping of a third medium via a permeable stamp matrix. In a second embodiment of the present invention, this problem is solved by providing a patterned stamp surface that controls the thickness of the third medium layer and allows excess medium to escape through drainage channels.

In an example of the second embodiment, a layer of third medium is trapped between a protrusion of the stamp and the substrate. The third medium is used to carry out deposition of molecules and to provide an environment for catalytic reactions. In a another example of the second embodiment, patterned stamp surfaces are provided in which recesses define molecular sized gaps. The gaps allow transfer of DNA oligomers and polymerase chain reactions (PCR) at desired locations. In both these examples, the target substrate is preferably within the length of the molecule to facilitate efficient interaction.

Referring now to FIG. 4A, in an example of the first embodiment, a stamp 26 comprises active vias 28 and recesses 30. Referring to FIG. 4B, the vias 28 and recesses 30 are filled with a polymer gel matrix 32 permeable by a third medium, such as water or other buffer material. Plugs are thus formed in the vias 28 and recesses 30. By uptake of the third medium, the gel 32 swells to an equilibrium state such that the gel 32 protrudes beyond the surface 33 of the stamp 26. The swilling may be performed in a 100% vapour phase environment. The stamp 26 may then be stored in such an environment to prevent subsequent drying of the gel 32. Because the gel 32 within the stamp 26 is held in another material, the metrology of the stamp 26 is not affected by the swelling. Referring to FIG. 4C, and particularly the arrows therein, the protrusions of gel 32 are then selectively addressed via a stencil 34 and filled with the molecules for patterning. Each via 28 and recess 30 may be loaded with different molecules to be transferred. Because the plugs of gel 32 in the vias 28 and recesses 30 are isolated, there is no interdiffusion between neighboring plugs. With a via thickness of 10 µm and a loading with 1-weight-percent of molecules, the amount of material stored in the stamp 26 is sufficient to print several hundred monolayers of molecules. Referring to FIG. 4D, the stamp 26 is now brought into contact with a substrate 36 to transfer the desired amount of material. The stamp 26 need not be immersed in liquid, thus reducing printing complexity. The gel 32 holding the third medium provides full solvatation of the molecules and also a good environment for a chemisorption reaction. The permeability of the gel 32 allows any third medium trapped between the stamp 26 and the substrate 36 to escape through the gel 32. This avoids separation of stamp 26 and substrate 36 by the third medium. Inking of the different vias 28 and recesses 30 may be performed via sequential methods such as pipetting, pin spotting, or ink jet spotting. Semi-parallel methods based on fluidic networks may also be used to provide selective addressing. Other examples of this embodiment may comprise only vias 28. Similarly, further examples of this embodiment may comprise only recesses 30. There is no additional layer of third medium trapped between stamp 26 and substrate 36. However, the third medium can be in contact with the substrate 36 as a majority component of the gel 32. Thus, the gap between stamp 26 and the substrate 36 need not be controlled. Another application of stamps with gel protrusions permeable by a third medium and not fully swelled is the combined concentrating and printing of diluted solutions. This is generally useful for detection of molecules and particularly useful for detection of pollutants at extremely low concentrations. Examples of pollutants include metal ions such as $Pb^{2+}$, $Hg^{2+}$, $Zn^{2+}$, etc. Detection can then be achieved by measuring adhesion during removal. Other detection schemes are possible.

Figure 5B:
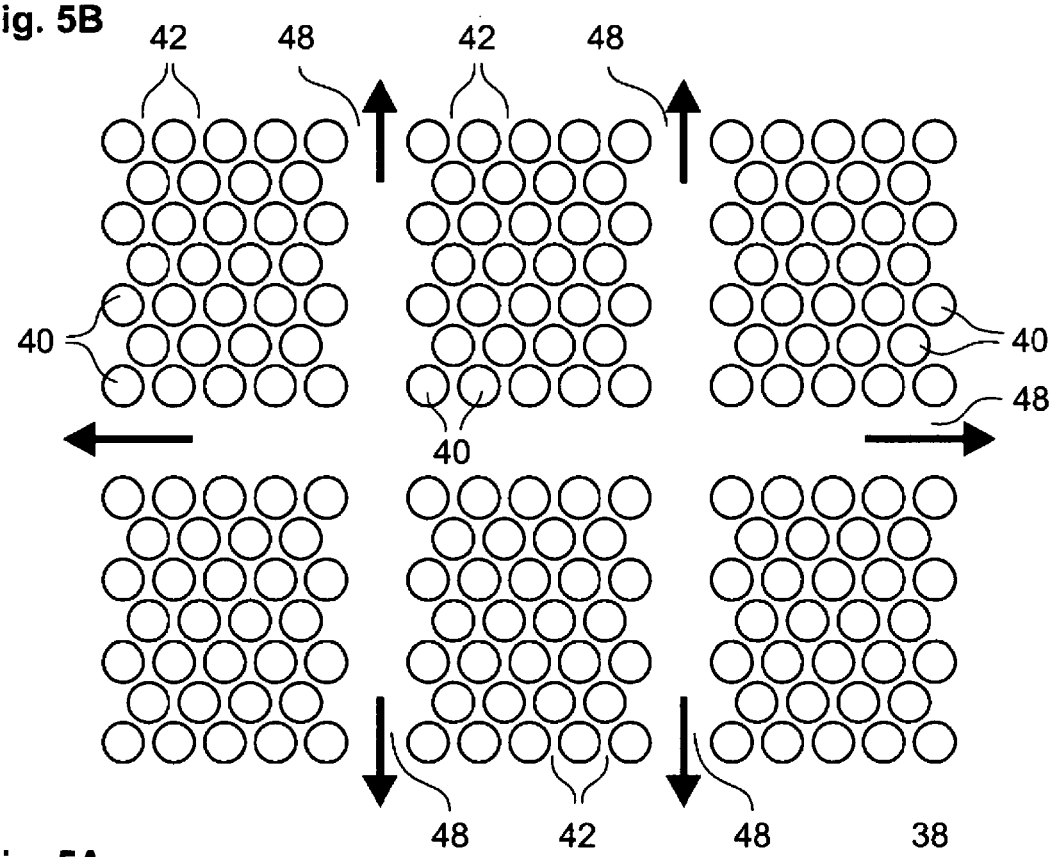
FIGS. 5A to 5F are cross-sectional and plan views of another stamp embodying the present invention.
Figure 5A:
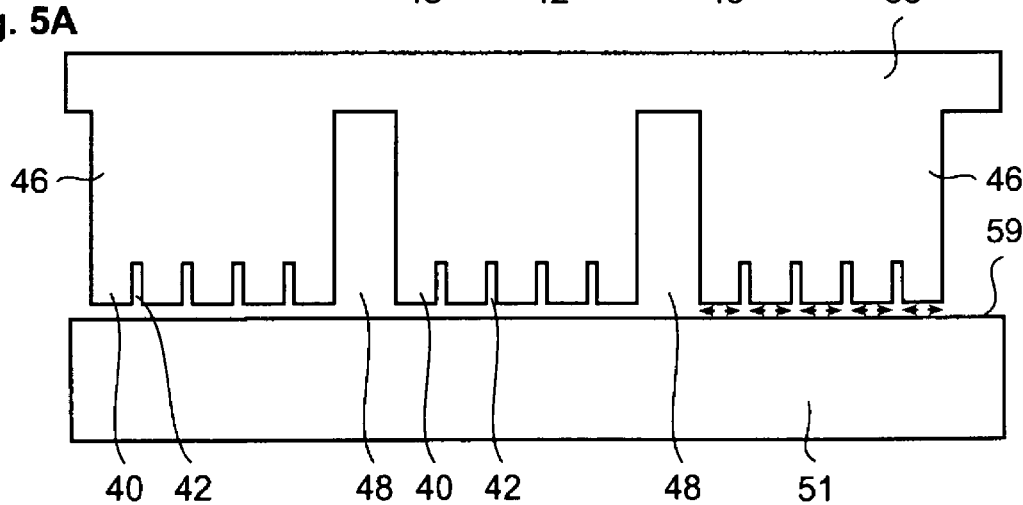
Figure 5C:
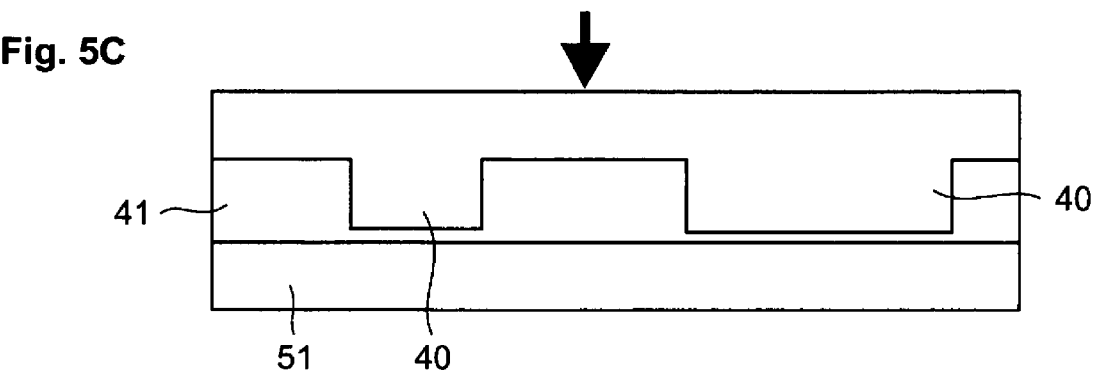
Figure 5D:
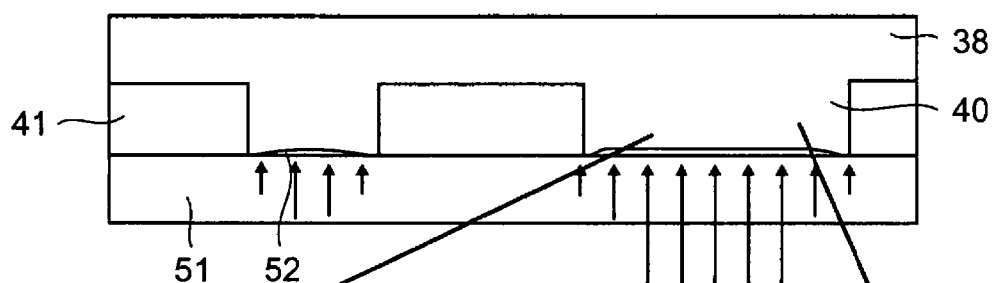
Figure 5E:
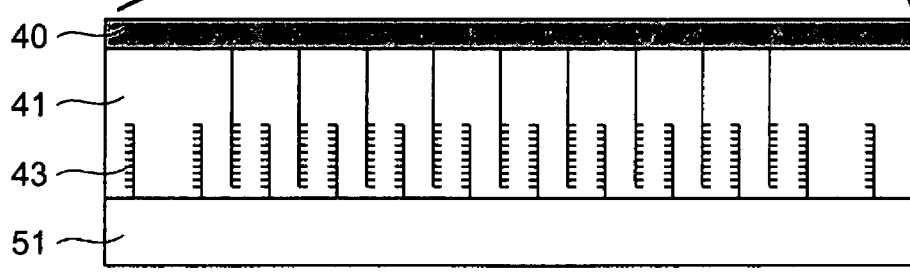
Figure 5F:
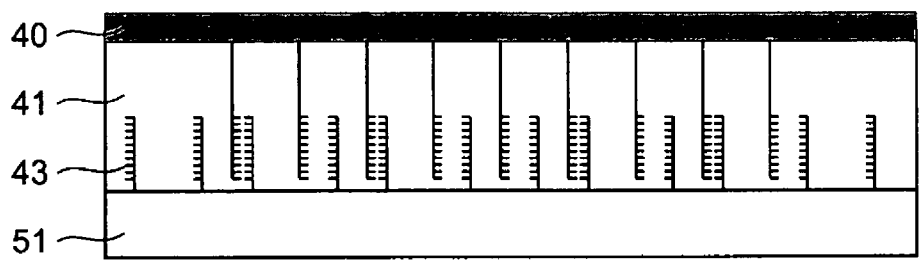

Referring to FIG. 5A, in an example of the second embodiment, a hydrophilized elastomeric stamp 38 has an array of protrusions 46 with a high fill factor. Each protrusion 46 is subdivided into smaller protrusions 40 separated by recesses 42 acting as small channels to guide excess third medium away before printing contact with the hydrophilic surface 50 of a substrate 51 is established. Referring to FIG. 5B, the smaller protrusions 40 can be circular, rectangular, or of other cross section, in square, hexagonal, or other packing. The contact area of the smaller protrusions 40 is maximized while simultaneously leaving the smaller channels 42 to form an open linked network. The larger protrusions 46 are separated by larger drainage channels 48 in communication with the smaller drainage channels. In a preferred example, the protrusions 40 have a size of 10 µm and a height of 3 µm. Other dimensions are possible. FIG. 5C shows protrusions 40 approach the substrate 51 in the presence of the third medium 41. FIG. 5D shows local trapping of third medium 41 in shallow pockets between the protrusions 40 and the substrate 51. The size of the pockets 52 may be 80% of that of the protrusions 40. The depth of the pockets 52 is proportional to the square of the size of the protrusions 40. FIG. 5E shows molecules 43 attached to the substrate 51 and to the protrusion 40 within one of the pockets. FIG. 5F shows interaction between the molecules 43 attached to the substrate 51 and the molecules 43 attached to the protrusion 40 within one of the pockets. For molecular transfer and controlled execution of a chemisorption reaction, a gap between the stamp 38 and the surface 50 of the order of 2 nm is usually sufficient. According to an experimentally determined ratio of 750 between protrusion size and gap thickness, patterns having a size of 1.5 μm is suitable. The recesses 42 providing the drainage channels on the stamp 38 are mutually connected to drain the third medium away into the larger channels 48. Different protrusions 40 on the stamp 38 can transfer different molecules by selective inking. Sequential methods such as robotic pipetting, pin spotting, or ink jet spotting may employed for such inking. Semi-parallel methods related to fluidic networks are equally applicable.

Figure 6A:
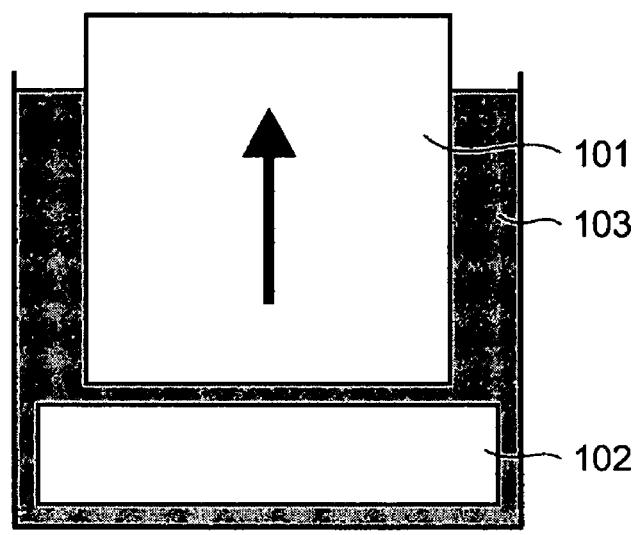
FIGS. 6A to 6C are cross sectional views of an adhesion sensor.
Figure 6B:
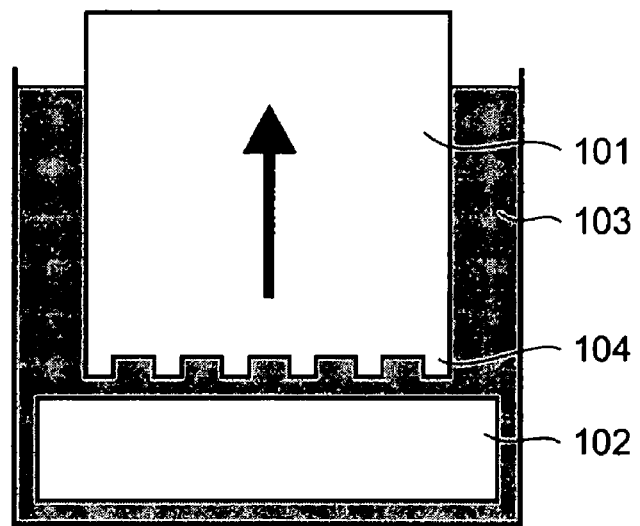
Figure 6C:
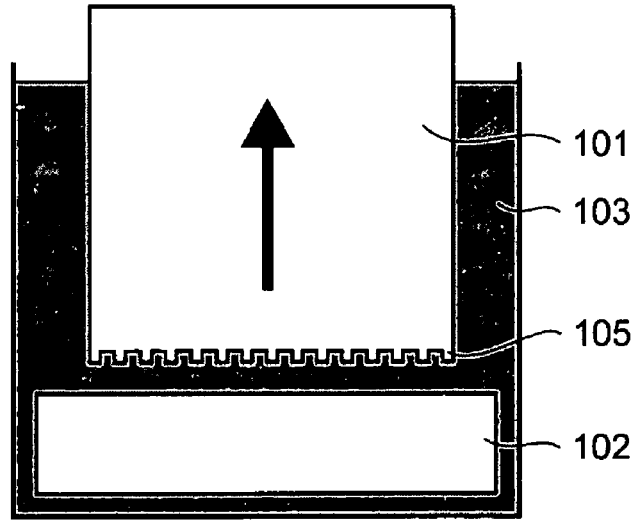

FIG. 6 shows adhesion force between stamp 101 and substrate 102 in a third medium 103 as a function of stamp substructures. Referring to FIG. 6A, large surfaces do not trigger noticeable molecular interactions. Referring to FIG. 6B, medium (10 μm) protrusions 104 trigger small interaction forces. Referring to FIG. 6C, small (<10 μm) protrusions 105 show strong interactions.

Figure 7A:
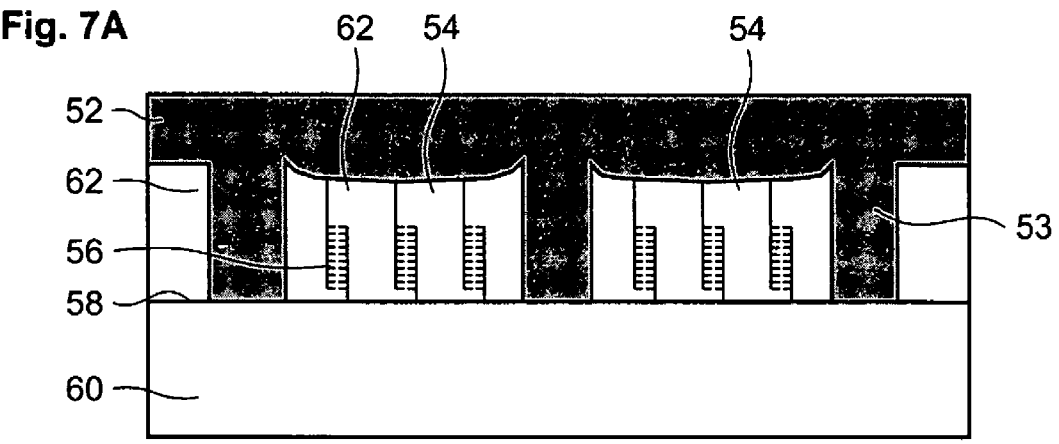
FIGS. 7A to 7D are cross sectional and plan views of yet another stamp embodying the present invention.
Figure 7B:
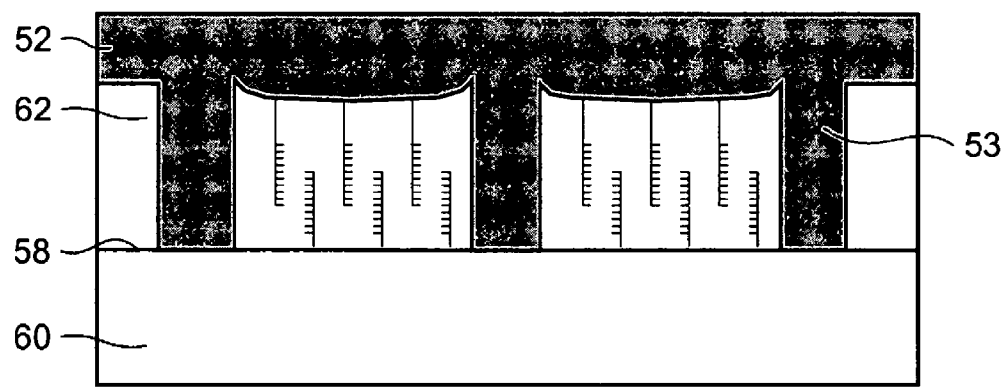
Figure 7C:
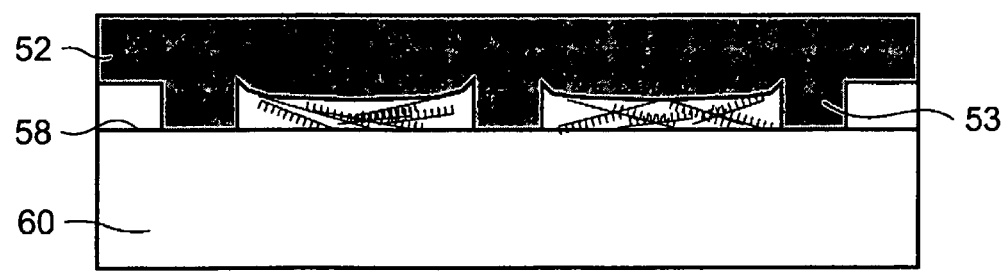
Figure 7D:
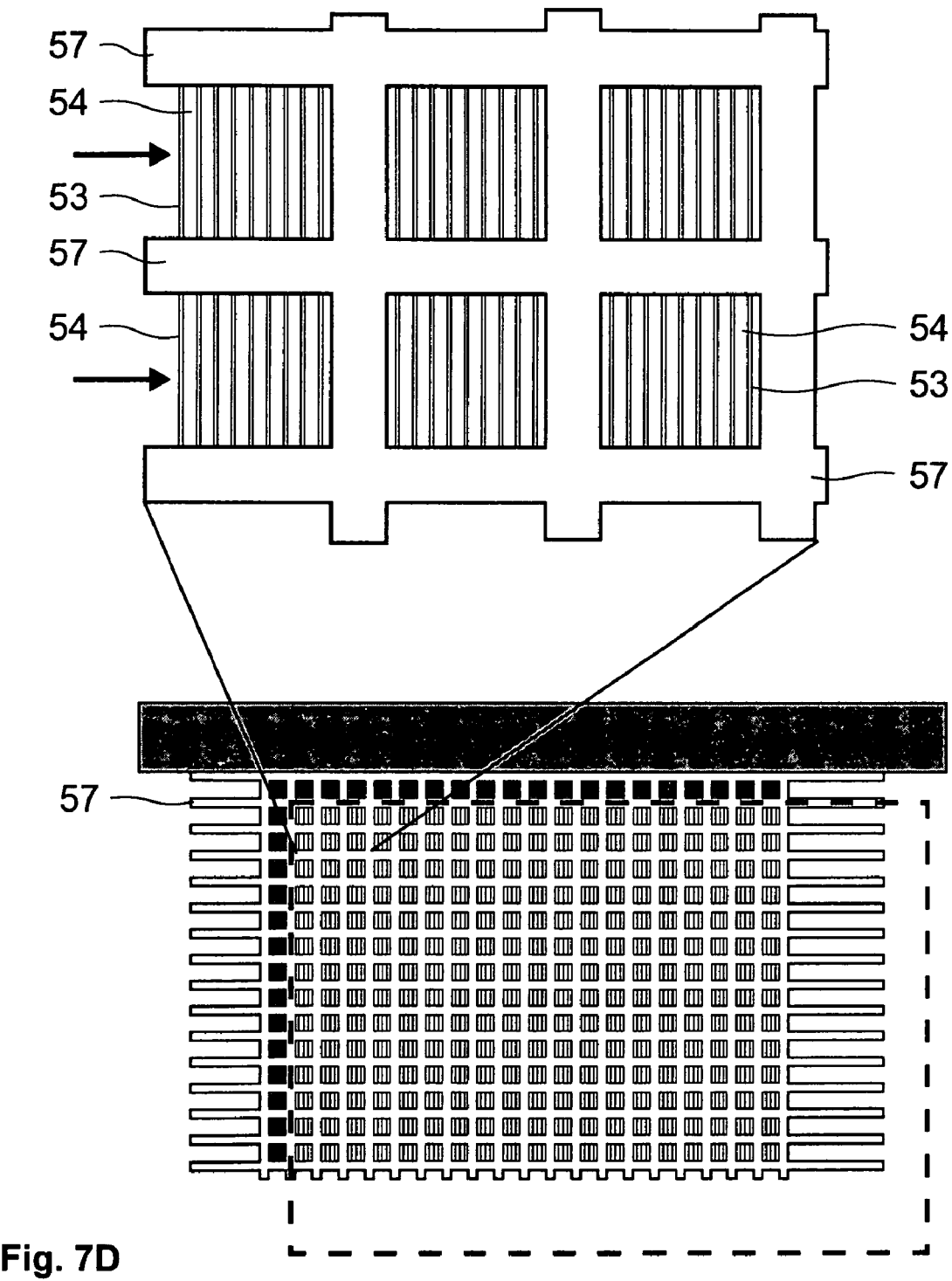
Figure 8A:
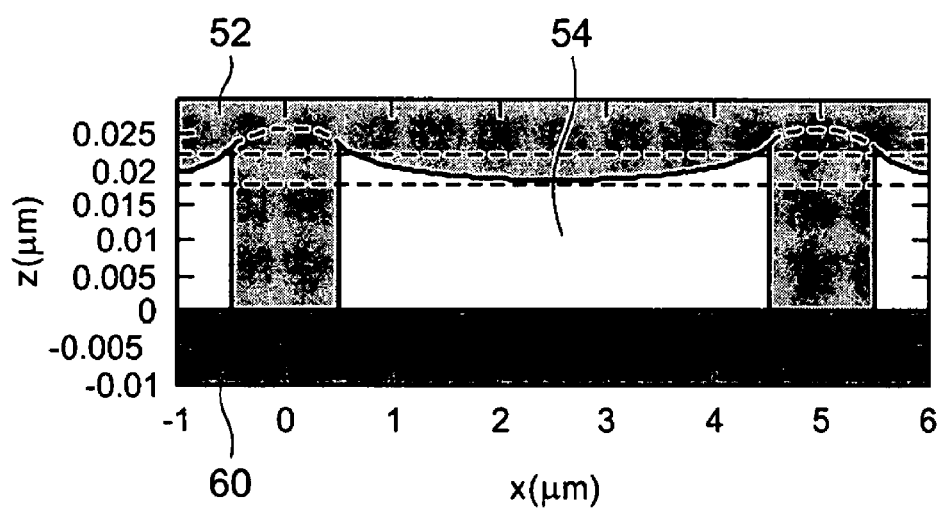
FIGS. 8A and 8B are cross sectional views of stamps having shallow channels.
Figure 8B:
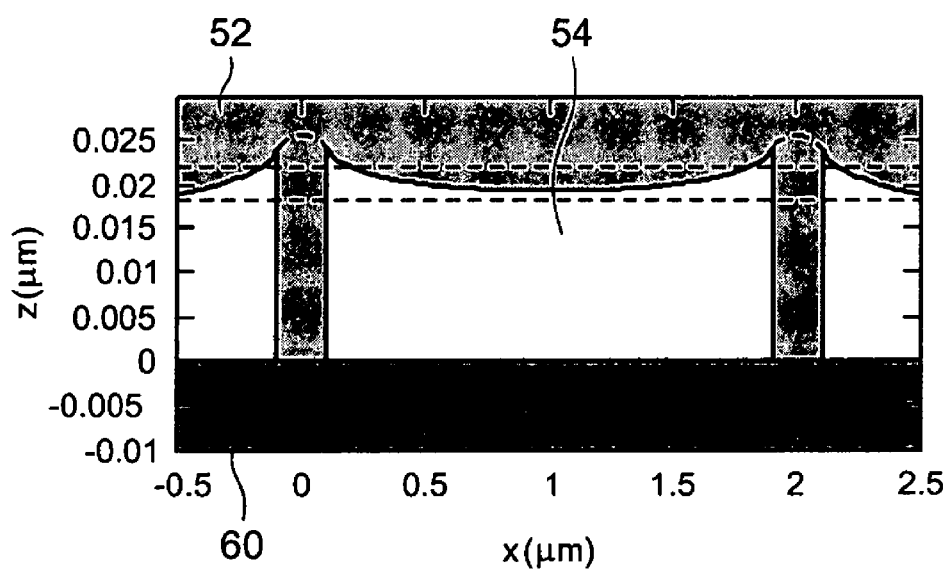

Referring now to FIG. 7A, in another example of the second embodiment, a stamp 52 has shallow elongate parallel channels 54 formed therein. The channels 54 are separated by intervening walls 53. In preparation for operation, the channels 54 are coated with particular molecules 56. In operation, the channels 54 form active zones in which molecules 56 on the stamps 52 are brought into proximity with molecules 56 on the surface 58 of a substrate 60 when the stamp 52 is brought into contact with the substrate 60. The molecules 56 on the stamp 52 and the substrate 60 interact within each channel 54 when the stamp 52 is in contact with the substrate 60 in presence of a third medium 62. For biomolecular interactions, the third medium 62 may be water or a water based solution containing other solvents, buffer ions, nucleosides and/or enzymes. The channels 54 define a layer of the third medium 62 with sufficient thickness to allow performance of a biochemical process. The stamp 52 is preferably made from a thin layer of elastic material to provide large area molecular contact. An externally applied load is applied such that any sagging induced is sufficiently small to provide a substantially uniform gap thickness in each depression 54. The load can be regulated to adjust the gap. Referring to FIG. 7B, if the load is too small, the gap may be too large to permit interaction between the molecules on the stamp 52 and molecules on the substrate 60. Similarly, referring to FIG. 7C, if the load is too large, the stamp 60 may collapse and gap may be too small to permit interaction between the molecules on the stamp 52 and molecules on the substrate 60. Referring to FIG. 7D, in a particularly preferred example, a stamp 60 is patterned via contact lithography for producing a 25 mm biochip. The channels 54 are 4 μm wide and the separating walls 53 are 60 μm long, 1 μM wide, and 25 nm high. Excess third medium 62 displaced during printing is collected by 40-μm-wide and 40-μm-deep drainage channels 57 and drained away on a macroscopic scale by several millimeters. The drainage channels 57 define active zones of the stamp occupied by groups of the smaller channels 54. The desired channel height depends on the molecules involved and can vary from e.g. 2 nm to 200 nm. In general, if the molecular length is 20 nm then a channel of >20 nm is too large and a channel of <5 nm is too small. The drainage channels 57 permit printing of a relatively large substrate 60 without limiting effective fill factor. The stamp 52 may be molded in Sylgard® 184 from a master with a compression modulus of 3 Mpa. The master may be fabricated via lithography methods such as projection lithography and e-beam lithography. Such a stamp 52 may be pressed onto the surface 58 with an average pressure of around 3 kPa distributed over the area of the stamp 52. In this example, drainage may require around 10 seconds, during which the larger channels guide 57 away the third medium over around 70 mm. FIG. 8A shows the height profile across a 4-μm-wide and initially 25 nm high channel 54 molded in Sylgard® 184 with a compression modulus of 3 Mpa. The channel 54 was placed in contact with a substrate 60 under 3000 Pa pressure. The channel 54 is compressed to 22 nm at the edges and to 18 nm in the center. A ±10% gap width accuracy is achieved. This is consistent with the length tolerance for hybridization on oligomers. To tune the stamp 52 to a different system of molecular interaction, the width of the channel 54 can be adjusted by changing the load. A reduction of the load to 1500 Pa, for example, increases the minimal channel width from 18 to 22 nm. In a second example, the stamp 52 comprises 10×10 μm sized active zones each having 6 12 μm long 200 nm wide and 25 nm high supporting walls 53 separating 1800 nm wide shallow channels 54. 8 μm deep and 8 μm wide drainage channels 57 direct excess third medium such as water to the boundary of the stamp 52 around ±10 mm away. The stamp 52 may again be molded from Sylgard® 184 with a Young's modulus of 3 MPa and pressed onto the surface with an average pressure of 5 kPa distributed over the stamp 52. The time needed to displace excess water to the boundary with the selected pressure may be again around 10 seconds. FIG. 8B shows a height profile across such a 1800 nm wide and initially 25 nm high channel 54. In some embodiments of the present invention, materials other than Sylgard® 184 and possibly harder may be used.

Figure 9:
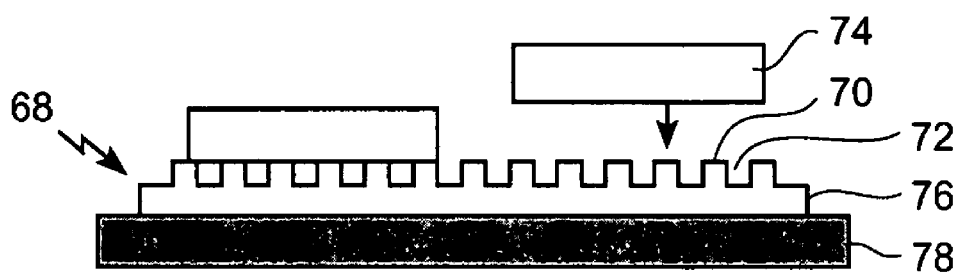
FIG. 9 is a cross-sectional view of a bonding pad embodying the present invention.

Referring now to FIG. 9, in another embodiment of the present invention, a bonding pad 68 comprises flat elastomeric adhesive protrusions 70 separated by drainage channels 72. The channels 72 permit a third medium such as air to escape when a flat object 74 is placed on the pad 68 at high speed. At high speed, a pressure of greater than 1 bar builds up in the third medium at a gap height of 0.2 μm or more. The protrusions 70 extend from an elastomeric layer 76 supported by a backplane 78. The elastomeric layer 76 may be a siloxane rubber such as poly(dimethylsiloxane). This material relaxes to its original shape after release of mechanical stress. The natural adhesive proprieties of the surface may be enhanced with adhesives or other surface activation. The backplane 78 is a flat layer such as thin glass, metal, silicon or polymer, holding the elastomeric layer 76 accurately in place and preventing lateral and vertical distortions. The pad 68 accurately holds the parts 74 in place in a coplanar fashion to allow accurate robotic transfer of the parts 74 to a carrier substrate or to allow parallel processing of the parts 74. Removal of the parts 74 from the pad 68 is typically performed by peeling to avoid potential overloading of the parts 74 or the pad 68. Such overloading may occur in other separation techniques such as, for example, vertical pulling. An example application is thin film head slider fabrication. Present sliders 74 have typical dimensions of 1×1 mm$^2$ and can be accurately placed onto a substrate by robot at vertical speeds of 10 mm/s. Accurate results are achieved with elastomeric protrusions 70 of 10 to 20 μm width and separated by drainage channels 76 of typically 1-5 μm diameter. The channels 76 prevent trapping of air pockets between the sliders 74 and the pad 76 by allowing air to escape. Air pressure remains moderate, exceeding 1 bar only at distances closer than 150 nm. Stamp deformation is low. The trapped air is negligible and any residual air can be quickly dissipated through the pad 68. Elastomeric silicone rubbers are surprisingly permeable for small amounts of gases. Without the drainage channels 76, a pressure of greater than 1 bar builds up when a slider 74 approaches the pad 68 closer than 2 μm. Air pockets are then trapped under the slider 74. The air pockets distort the pad 68 in an unpredictable way and create vertical and/or lateral distortions.

Figure 10A:
FIG. 10A is a cross sectional views of a printing cylinder.
Figure 10B:
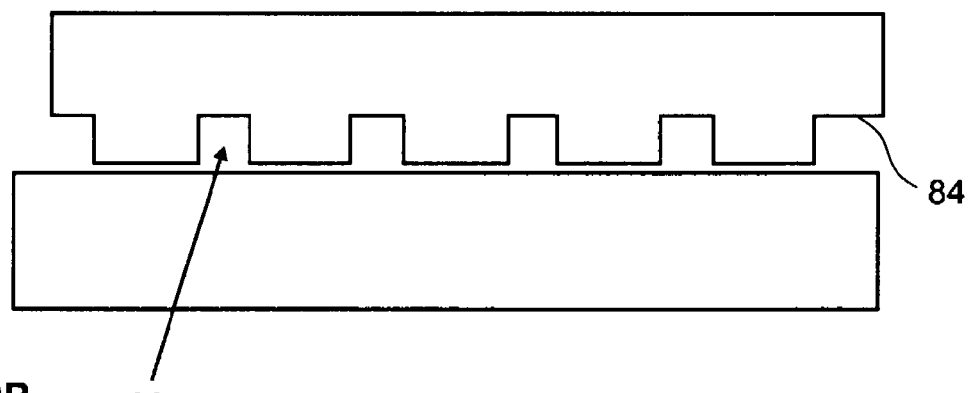
FIG. 10B is a cross sectional view of a printing cylinder embodying the present invention.

Controlled layers of water are important in offset printing processes for reliable print contrast. Dedicated topographic patterns improve control over ink buffering, water buffering and tangential transport of liquid. To maintain print contrast, it is desirable to avoid longer distance net transport. FIG. 10A shows an side view of a typical surface 80 of a printing cylinder 82 with random roughening. FIG. 10B is a section through a micro structured surface 84 in which percolation paths 86 are disposed. With the advent of low-cost micro structuring, printing processes can be made more efficient by exchanging random roughening for well defined structures. The well defined micro structures optimize tangential and axial flow without reducing fill factor. This, is especially important for printing operations onto impermeable surfaces such as metal, glass, or ceramic where excess liquid cannot penetrate or otherwise escape the printing gap.

Figure 11A:
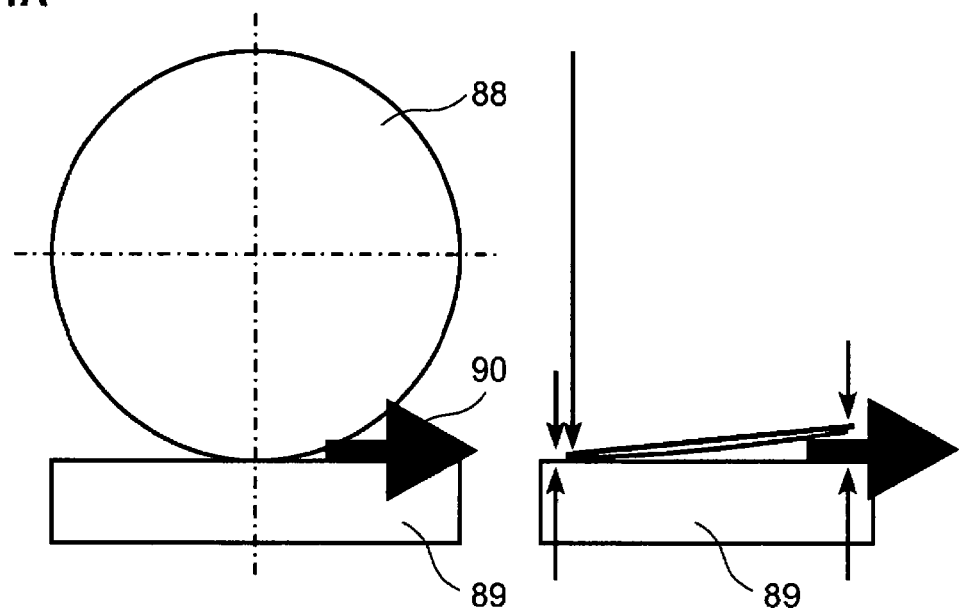
FIG. 11A is a side view of a printing cylinder.
Figure 11B:
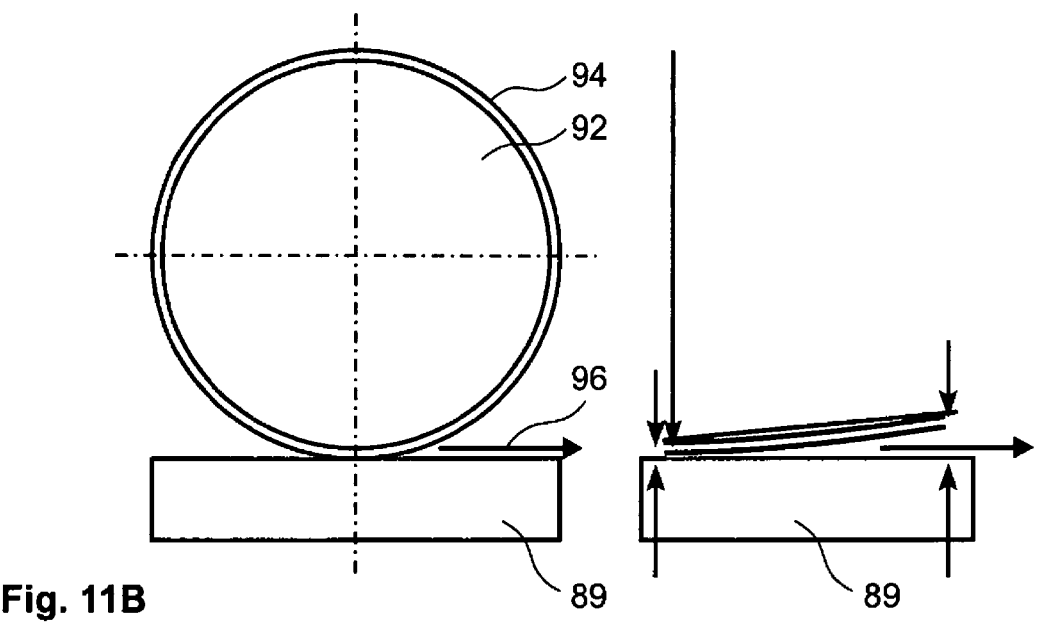
FIG. 11B is a side view of a printing cylinder embodying the present invention.

Topographic patterns like those herein before described provide improved control over ink buffering, water buffering and tangential transport of liquid. In a preferred embodiment of the present invention, small trenches are formed in one of the contact surfaces to create a connected fluid mesh. The mesh permits high printing speeds, allows larger parameter ranges for inking, allows thicker printed layers, reduces dependency of color mixing on printed patterns, and simplifies damping and inking. Topographic patterns for controlled water flow are important in flat printing such as biochip patterning and also in printing from stamps wrapped onto cylinders to form rolling contacts. FIG. 11A shows flow resistance of fluid escaping a smooth advancing cylinder 88. The resistance is represented by the large arrow 90. This resistance generates pressure. The pressure lifts the cylinder 88 in a similar manner to aqua planning of car tires. FIG. 11B shows that an advancing cylinder 92 having a circumferentially disposed drainage pattern 94 creates a smaller pressure in the liquid as indicated by the smaller arrow 96. The cylinder 92 is thus less susceptible to aqua planing. Thus, faster printing speeds can be achieved. In a rolling contact, the third medium is displaced ahead of the cylinder or laterally if there is excess medium only partially along the cylinder. The right half of FIG. 11 shows the gap between the cylinder surface and the substrate 89 as a function of the distance from the cylinder axis and its tangential approximation. In FIG. 11A, the fluid resistance is high because the remaining gap is small. In FIG. 11B, the fluid resistance is smaller because of channels 94 formed in the surface of the cylinder 92.

Figure 12A:
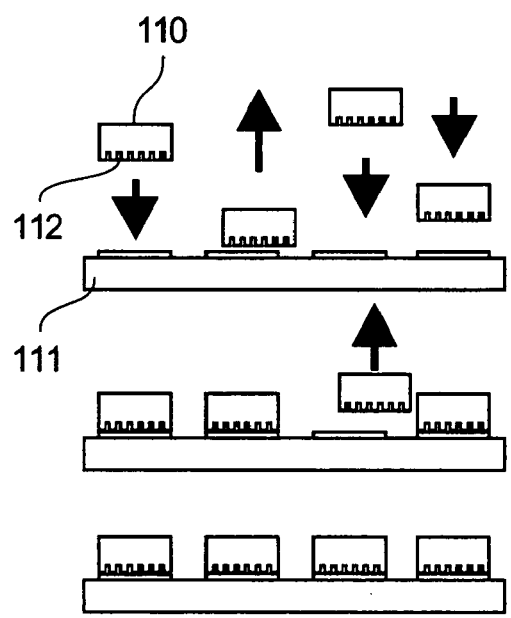
FIG. 12A is a block diagram showing spontaneous interaction between a particle and a flat surface with patterning; and, FIG. 12B is a block diagram showing spontaneous interaction between a particle and a flat surface without patterning.
Figure 12B:
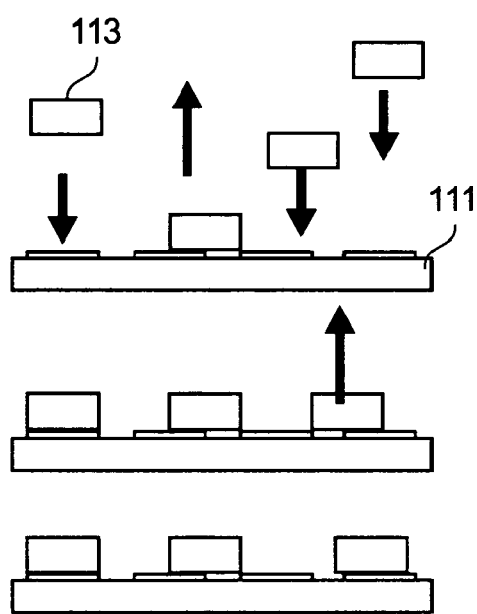

In another embodiment of the present invention, self-assembly of micrometer sized particles 110 using specific molecular interaction involves patterning of either a substrate surface 111 or contacting surface 112 of the particles 110 with structures herein before described. The patterned contact surfaces 112 improve the binding speed. In addition, the patterned contact surfaces 112 allow faster separation of unbound or partially bound particles 110. This improves overall speed of self-assembly process and improves specificity of interaction over particles 113 with no patterned surface 112. FIG. 12A shows particles 110 having a patterned surface 112 interacting specifically with a surface 111. In FIG. 12B, there is shown a slower and less specific interaction between the surface 111 and particles 113 without a patterned surface. The receiving surface 111 can be patterned instead of the particles 110.

What is claimed is:

1. A method comprising transferring a pattern from an elastic stamp to a substrate in the presence of a third medium, the step of transferring comprising: bringing the stamp into contact with the substrate while controlling a layer of the third medium between the stamp and the substrate to a predetermined thickness by filling vias and recesses formed in the stamp with a component having an affinity for the third medium, and guiding excess third medium away from the surface of the stamp.

2. A method according to claim 1, wherein the substrate is rigid.

3. A method according to claim 1, wherein the substrate is impermeable.

4. A method according to claim 1, wherein the third medium comprises one or more of gas, water, solvent, polymer, emulsion, and sol-gel precursor.

5. A method according to claim 1, wherein the step of controlling comprises avoiding trapping of the third medium via a stamp matrix being permeable to the third medium.

6. A method according to claim 1, wherein the step of controlling comprises allowing a nanometer sized gap in the stamp to get filled with the excess third medium.

7. A method according to claim 1, wherein the step of controlling comprises providing a patterned stamp surface having channels to drain the excess third medium.

8. A method according to claim 1, wherein the component is hydrophilic.

9. A method according to claim 8, wherein the component comprises a gel.

10. A method according to claim 9, wherein the gel is swellable by the third medium.

11. A method according to claim 10, wherein the step of controlling comprises swelling the gel with the third medium to form protrusions in the stamp.

12. A method according to claim 1, wherein the excess third medium is trapped in a shallow lens-like pocket between the stamp and the surface of the substrate.

13. A method according to claim 1, wherein the step of controlling comprises trapping the excess third medium in a pocket between the stamp and the substrate.

14. A method according to claim 1, wherein the stamp comprises channels.

15. A method according to claim 14, wherein the channels define molecular sized gaps between the stamp and the substrate.

16. A method comprising employing the method of claim 1 for a process taken from a group of processes consisting of:
    printing biological molecules on a surface;
    printing dyes on a surface;
    printing catalysts on a surface;
    printing acids or bases on a surface;
    printing of radical initiators on a surface;
    detection of molecules through proximity by fluorescence resonance transfer;
    purification and concentration of reactants;
    in an offset printing process;
    in a rolling contact process; or
    any combination of these processes.

* * * * *